United States Patent
Varma et al.

(10) Patent No.: US 10,017,583 B2
(45) Date of Patent: Jul. 10, 2018

(54) SYNTHESIS OF NANOSTRUCTURED CARBOXYCELLULOSES FROM NON-WOOD CELLULOSE

(71) Applicant: Council of Scientific & Industrial Research, New Delhi (IN)

(72) Inventors: Anjanikumar Jyotiprasad Varma, Pune (IN); Priyanka Radheyshyam Sharma, Pune (IN); Dhiman Sarkar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 318 days.

(21) Appl. No.: 14/895,590

(22) PCT Filed: Jun. 3, 2014

(86) PCT No.: PCT/IN2014/000373
§ 371 (c)(1),
(2) Date: Dec. 3, 2015

(87) PCT Pub. No.: WO2014/195971
PCT Pub. Date: Dec. 11, 2014

(65) Prior Publication Data
US 2016/0130368 A1     May 12, 2016

(30) Foreign Application Priority Data

Jun. 3, 2013 (IN) .......................... 1658/DEL/2013
Sep. 19, 2013 (IN) .......................... 2758/DEL/2013

(51) Int. Cl.
*C08B 11/12* (2006.01)
*A61K 31/717* (2006.01)

(52) U.S. Cl.
CPC ............ *C08B 11/12* (2013.01); *A61K 31/717* (2013.01)

(58) Field of Classification Search
None
See application file for complete search history.

(56) References Cited

U.S. PATENT DOCUMENTS

| 6,627,749 | B1 | 9/2003 | Kumar | |
| 2011/0020954 | A1* | 1/2011 | Shiomi | ................... C08B 1/006 436/530 |

FOREIGN PATENT DOCUMENTS

| RU | 2146264 C1 | 3/2000 |
| WO | 2007113835 A1 | 10/2007 |
| WO | 2012119229 A1 | 9/2012 |

OTHER PUBLICATIONS

Dineen et al., "The Effect of Oxidized Regenerated Cellulose on Experimental Infected Splenotomies," Journal of Surgical Research, Academic Press Inc., San Diego, CA, vol. 23, No. 2, Aug. 1, 1977, pp. 114-116.
Dineen et al., "The effect of oxidized regenerated cellulose on experimental intravascular infection," Surgery, Mosby, Inc., vol. 82, No. 5, Nov. 1, 1977, pp. 576-579.
International Search Report and Written Opinion in corresponding International Patent Application No. PCT/IN2014/000373, dated Oct. 1, 2014, 11 pgs.
Kumar, V. et al., "HNO3/H3PO4-NANO2 mediated oxidation of cellulose—preparation and characterization of pioabsorbable oxidized celluloses in high yields and with different levels of oxidation," Carbohydrate Polymers, Applied Science Publishers, Ltd., Barking, GB, vol. 48, No. 4, Jun. 1, 2002, pp. 403-412.
Scher et al., "Effects of oxidized cellulose and microfibrillar collagen on infection," Surgery, Mosby, Inc., vol. 91.No. 3. Mar. 1, 1982, pp. 301-304.

* cited by examiner

*Primary Examiner* — Christopher M Rodd
(74) *Attorney, Agent, or Firm* — Wood Herron & Evans LLP

(57) ABSTRACT

Disclosed herein is an improved process for the preparation of nanostructured oxidized/carboxy cellulose with high carboxy content and high yield, by subjecting non-wood, lignocellulose, sugarcane bagasse derived a-cellulose or cotton cellulose to oxidation at suitable temperature, wherein the particle shape is spherical, particle size of synthesized carboxy cellulose is in the range of 1-100 nm and degree of polymerization (DP) is in the range 50-70 Further the present invention provides pharmaceutical composition comprising of nanostructured oxidized/carboxy celluloses preferably 6-carboxy cellulose, and 2,3,6-tricarboxycellulose alone or in association with one or more pharmaceutically acceptable carrier(s) or excipient(s) for treatment of microbial infections. The carboxycelluloses were efficient in stabilizing multi-walled carbon nanotubes and single-walled carbon nanotubes in aqueous media.

7 Claims, 8 Drawing Sheets

Fig: 1
(a)
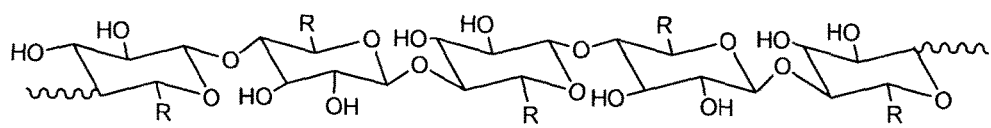
(b)
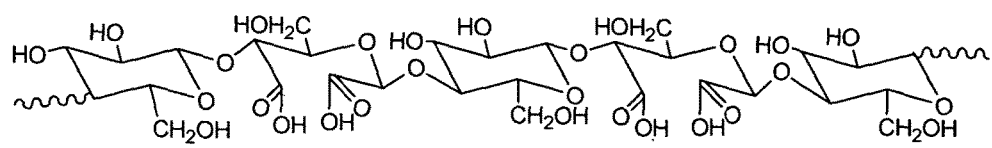
(c)
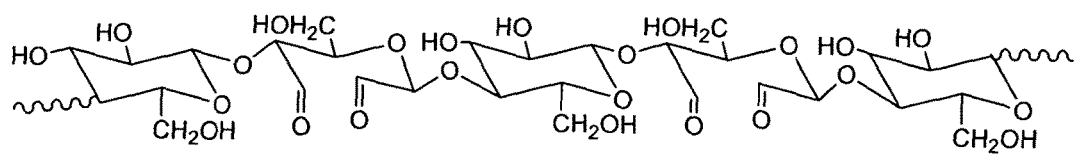
(d)
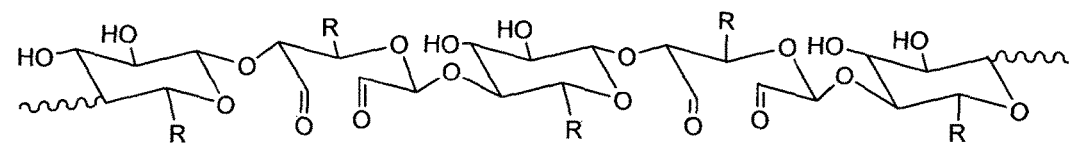
(e)
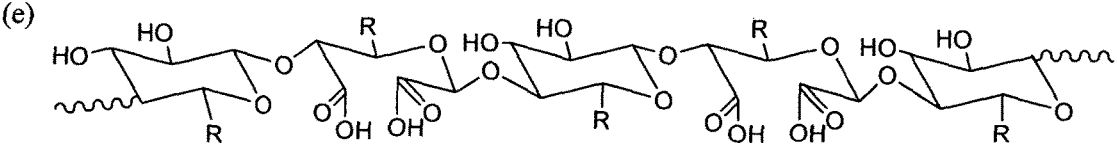

Fig:2
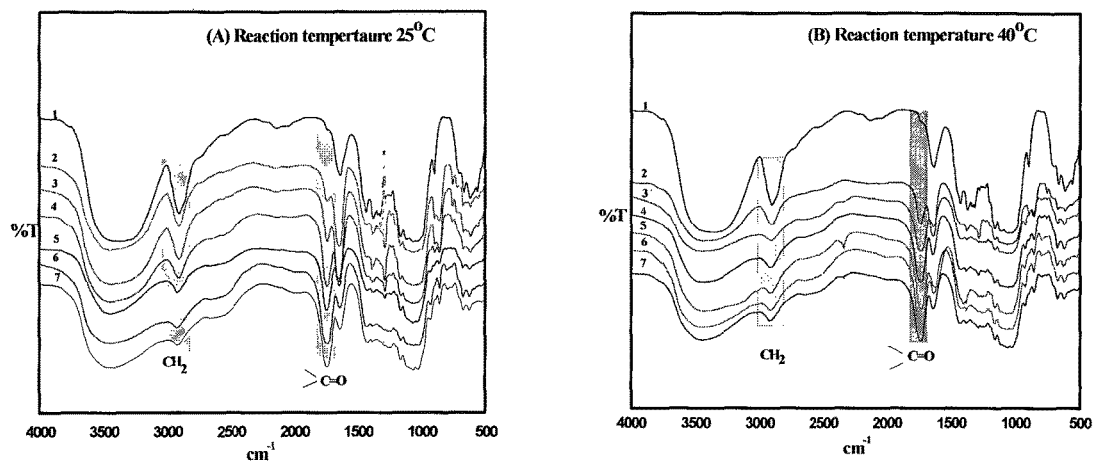
Fig:3
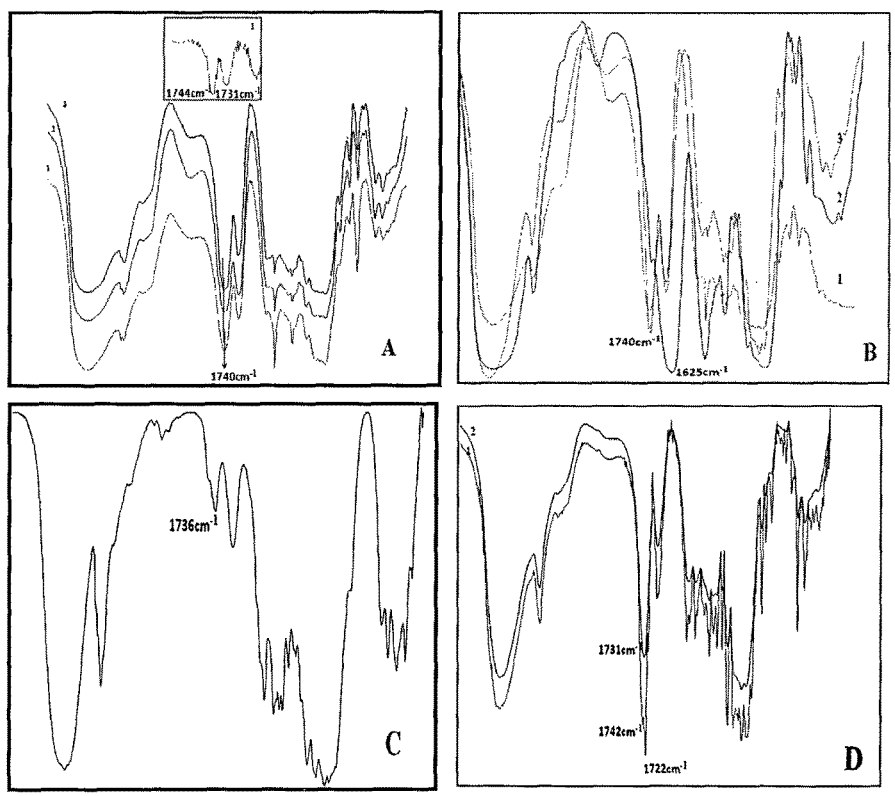

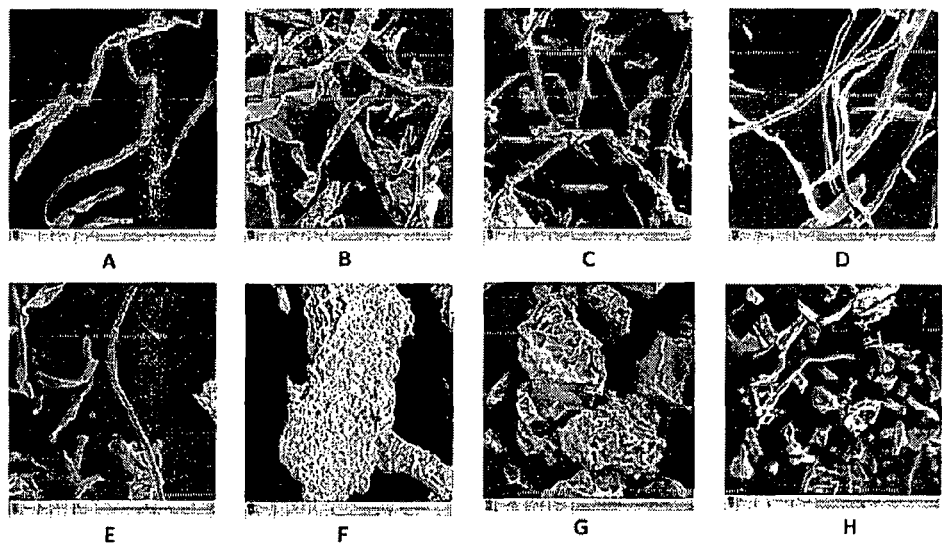
Fig: 4
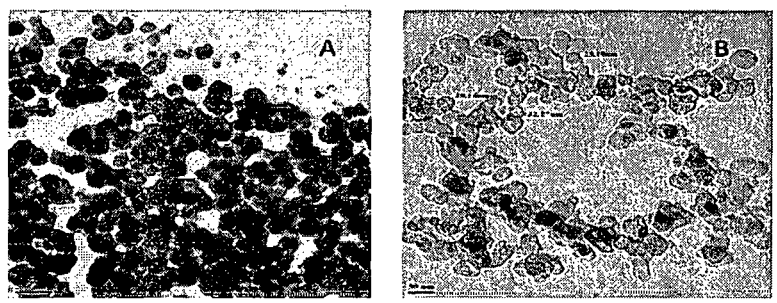
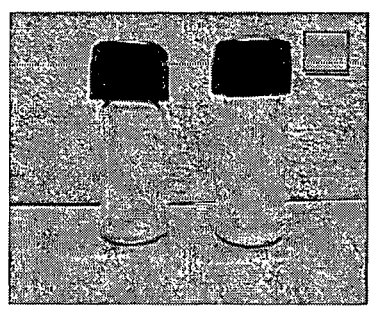
Fig: 5

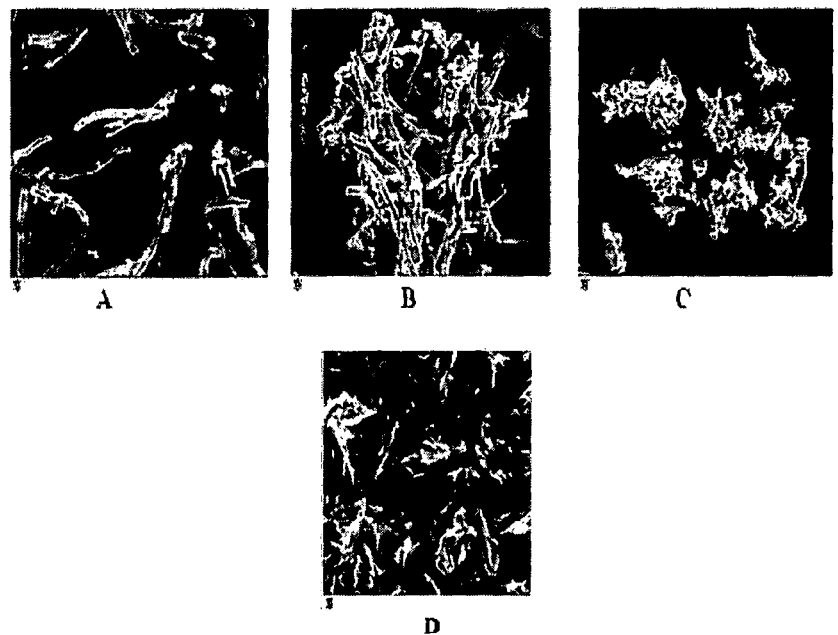
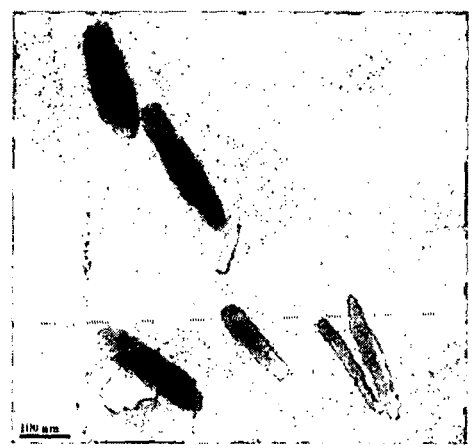
Fig: 6

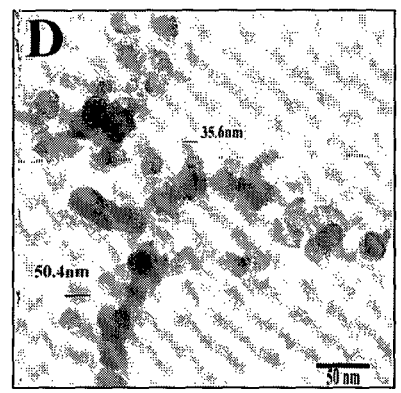
Fig. 7
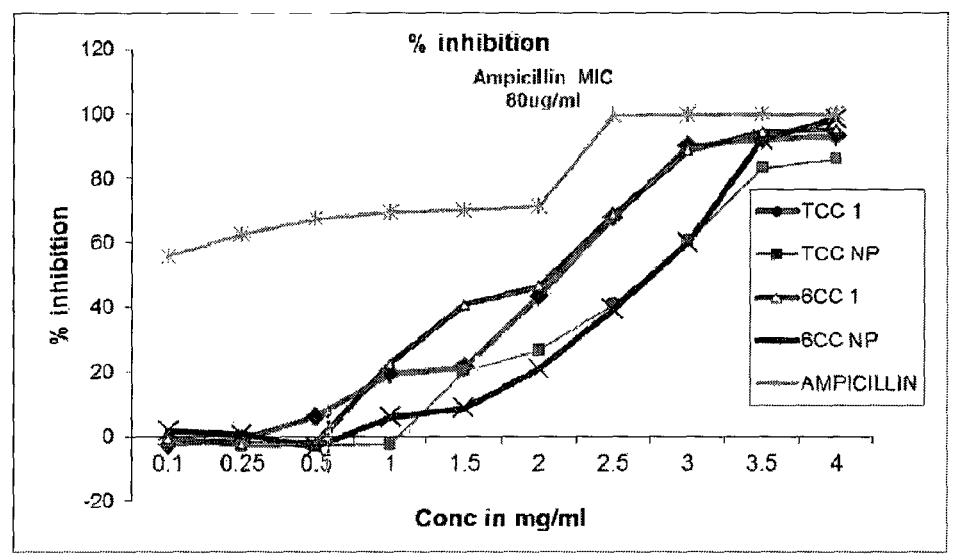
Fig: 8
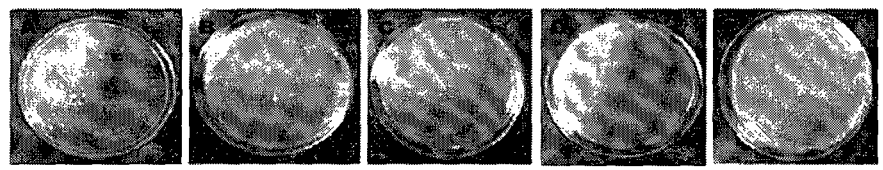
Fig: 9

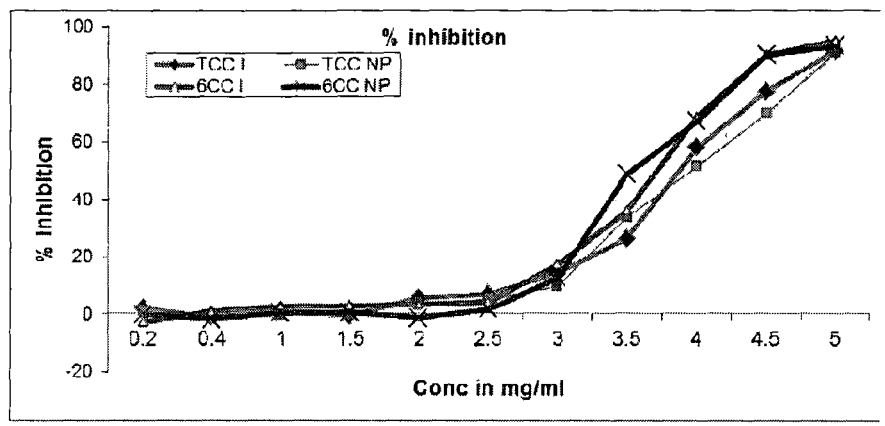
Fig: 10
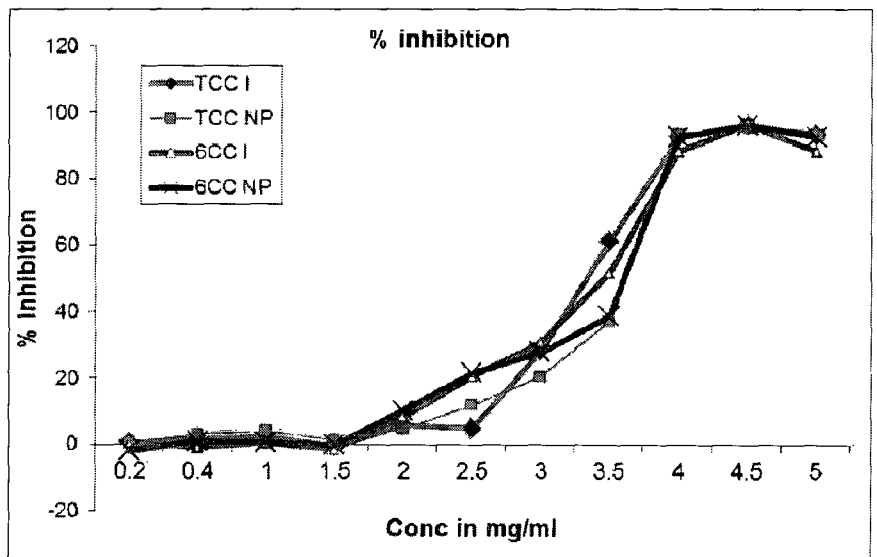
Fig: 11

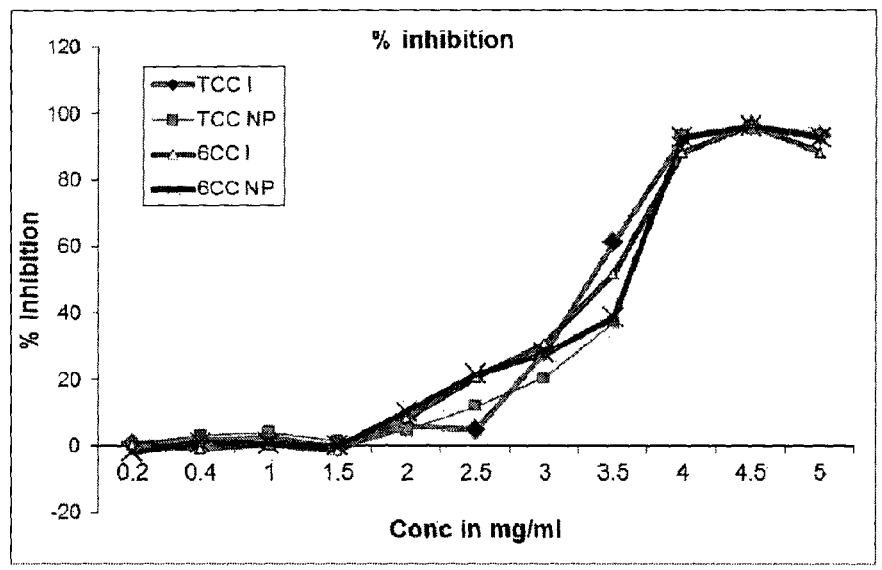
Fig: 12
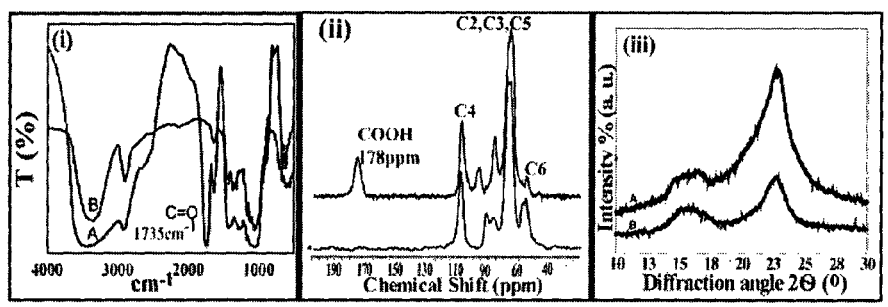
Fig: 13

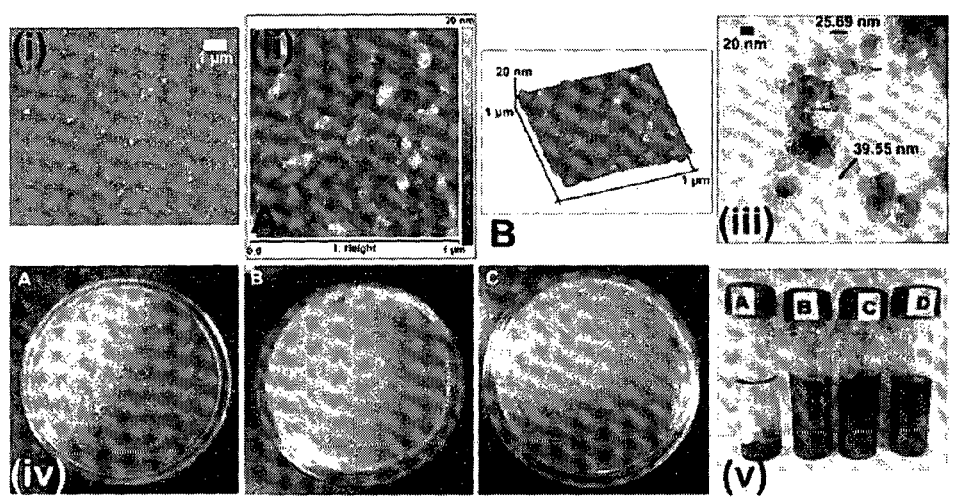
Fig: 14

SYNTHESIS OF NANOSTRUCTURED CARBOXYCELLULOSES FROM NON-WOOD CELLULOSE

TECHNICAL FIELD OF INVENTION

The present invention relates to an improved process for the preparation of nanostructured and spherical carboxy cellulose with high carboxy content and high yield. Particularly, the present invention relates to oxidation of non-wood, lignocellulose, such as sugarcane bagasse derived α-cellulose to carboxy cellulose wherein the particle size of synthesized carboxy functionalized celluloses is in the range of 1-100 nm.

Further the present invention relates to pharmaceutical composition comprising of nanostructured oxidized/carboxy celluloses, preferably 6-carboxy cellulose and 2,3,6-tricarboxycellulose either by themselves or in association with one or more pharmaceutically acceptable carrier(s) or excipient(s) for treatment of microbial infections.

BACKGROUND AND PRIOR ART

A very large, fraction of published literature on cellulose is devoted to softwood, hardwood, and cotton based cellulose, as these have higher molecular weights and are generally more suited for synthesizing various polymeric derivatives. Most cellulose production industries worldwide are still based on wood. Today, however, lignocellulose like sugarcane bagasse and other agricultural residues/non-woods derived celluloses are considered key raw materials for producing cellulose pulp, as they are annually renewable and considered more environment-friendly in comparison to wood.

Lignocellulose is composed mainly of cellulose, hemicellulose and lignin. The lignocellulose biomass or substrate is selected from agricultural residues such as corn stover and sugarcane bagasse, energy crops, wood residues such as saw mill and paper mill discards, and municipal paper waste.

Ververis C, et al. (2004) in industrial crops and products 19:245-254 discloses fiber dimensions, lignin and cellulose content of various plant materials and their suitability for paper production.

The high molecular weight wood material takes much more time to get replenished by nature, and separate land has to be set aside for their cultivation. On the other hand agricultural residues such as sugarcane bagasse and corn cobs do not need separate land as they are by-products of agricultural crops. While sugarcane bagasse and other non-wood biomass are known to possess lower molecular weights than wood celluloses, cellulose derived from these sources can substitute wood cellulose in several applications, particularly as carboxy celluloses in wound dressing gauzes, oxidized nanocelluloses for use in biocomposites, antimicrobial coatings, certain low molecular weight grades of high-volume soluble cellulose derivatives such as cellulose ethers like carboxymethyl cellulose, and also lead to newer applications, to replace petroleum derived products.

Low molecular weight oxidized celluloses have the advantage that they are more likely to swell or dissolve in organic solvents or dilute alkali solutions, thereby enabling their further facile transformations into several other new functional derivatives with new properties for further exploitation. Availability of industrial quantities of these celluloses will spur ever greater interest in re-visiting these materials as major industrial chemicals.

There exists a plethora of patents and papers published over the past decades on synthesis, manufacturing processes and applications of oxidized celluloses.

Accordingly, the oxidation of cotton linters, hardwood cellulose, and softwood cellulose is reported in some of the prior art. Synthesis of sodium nitrite based oxidation of cellulose have been reported since the 1940's, such as using gaseous nitrogen dioxide at 20° C., wherein a maximum carboxy content of 21.8% was obtained; using nitric acid with sodium nitrite system at 20° C., wherein a carboxy content of 18.32% which has been reported by Pigman W W in J Am Chem Soc 71:2200 (1949).

Another variation based on ortho-phosphoric acid (85%) and sodium nitrite was investigated in the art where specific C6 oxidation was difficult. A. C. Besemer et al. in *Cellulose Derivatives* Chapter 5, pp 73-82 Apr. 17, 1998 describes selective oxidation of the substrate at the 6-position of the glucose unit in presence of concentrated phosphoric acid with nitrite/nitrate. However, the reaction is not completely specific, since some oxidation at the secondary hydroxylic groups occurs. Further borohydride reduction of the product restores the diol configuration also β-elimination is avoided and thereby depolymerization. Oxidation with sodium hypochlorite and bromide as a catalyst and TEMPO as a mediator is also applicable to cellulose.

Further, oxidation of softwood pulp or cotton linters derived cellulose was carried by using $HNO_3/H_3PO_4/NaNO_2$ led to a maximum of 21.6% carboxyl content, while the $HNO_3/H_2SO_4/NaNO_2$ gave a maximum of 21.1% carboxy content.

U.S. Pat. No. 6,379,494 (Jewell, Richard A. et al.) reported use of TEMPO (2,2,6,6-tetramethylpiperidinyloxy free radical) as a primary oxidant and a hypohalite salt as a secondary oxidant for making carboxylated cellulose fibers from bleached northern softwood kraft pulp. Influence of oxidation time on selective oxidation of regenerated cellulose with $NO_2/CCl_4$ as oxidation system is disclosed in *Fibers and Polymers* May 2012, 13, (5), pp 576-581 by Ya Dong Wu. Oxidation of cellulose by acid-sodium nitrite systems is also reported by J. H. Arendt et al. *Journal of Polymer Science: Polymer Symposia* 42, 3, 1521-1529, 1973

On the other hand, Y W Sitotaw (2011) discloses the synthesis of carboxymethyl cellulose (CMC) from sugarcane bagasse, using sodium monochloroacetate and sodium hydroxide and a process for fractionating sugarcane bagasse into high α cellulose, xylan and lignin is reported in 1893/DEL/2007.

The conversion of tricarboxy cellulose from dicarboxy or dialdehyde cellulose compound is known in the literature. WO/2012/119229 discloses the method for preparation of 2,3,6-tricarboxycellulose (TCC) by 2,2,6,6-tetramethylpiperidine-1-oxyl (TEMPO) radical-mediated oxidation of periodate-oxidized chlorite-oxidized pulp (i.e. 2,3-dicarboxycellulose) at 60° C. for alternatively 5, 10, 5, 20 and 45 hours to liberate nanofibrillar cellulose (NFC). The preparation of haemostatic agent such as 2,3,6-tricarboxy cellulose by NO2 oxidation of 2,3-dialdehyde cellulose is reported by Sinha T J in Biomater Med Devices Artif Organs. 1984-1985; 12 (3-4):273-87.

Further, oxidation of dialdehyde cellulose gives di- or tricarboxy cellulose is disclosed by Tajima, K. in Journal Name: J. Appl. Polym. Sci.: Appl. Polym. Symp Journal vol 37; Conference: 9, May 1982. Russian Patent No. RU2146264 discloses the preparation of highly oxidized cellulose in presence of sodium periodate solution and solution of nitrogen oxides in carbon tetrachloride. The TEMPO (2,2,6,6-tetramethylpiperidine-1-oxyl radical)-mediated oxidation of wood celluloses to nanofibers 3-4 nm published by Isogai et al. 2011 *Nanoscale*, 2011, 3, 71-85).

Article in *Green Chem.*, 2012, 14, 300-303 by Robert J. Crawford discloses formation of shear thinning gels from partially C-6 oxidized cellulose nanofibrils. Jianguo Zhang et al in *Carbohydrate Polymers* 69 (2007) 607-611 reported procedure for synthesizing (cotton) hydrolyzed cellulose nanospheres with size ranging from 60 nm to over 570 nm.

Further nanofibers of oxidized celluloses are a subject of intense recent interest due to their potential for applications in severe areas high performance materials, such as gas barrier films, for example coatings for polyesters like poly (lactic acid) with very low oxygen permeability, hemostatically efficient materials with no pathological response, as a material to fractionate and purify proteins, enzymes, hemoglobins, hormones etc.

The larger nanoparticle sizes that have been obtained so far were likely to be due to the higher molecular weights of the starting cellulose, as they were based on tunicate and bacterial cellulose.

Vijay Kumar et al, (2002) in *Carbohydrate Polym* 48:403-412 discloses reaction of cellulose (cotton linter sheet) with a mixture of $HNO_3/H_3PO_4$—$NaNO_2$ (2:1:1.4, v/v/% w) at room temperature for different time intervals in to get oxidized cellulose with particle size ranging from 74 and 105 μm. However the inventors used lower molecular weights of non-wood celluloses as well as cotton cellulose and their oxidized derivatives which lead to smaller nanoparticles.

U.S. Pat. No. 7,662,801 (Kumar et al) reported use of a series of oxidized cellulose esters as a drug carrier in the development of biodegradable controlled and/or sustained release pharmaceutical, agricultural, and veterinary compositions, whereas Anderson et al (1946) Science 104 (2700), 301 reported substantial use of oxidized cellulose in surgery of the uterus in both cases the source of the cellulose is either softwood or hardwood pulp or cotton.

Functionalized nanocellulose technology appears to be destined to remain a key area of cellulose research due to innumerable possible applications.

In literature several interesting features were noted with progressive changes in oxidation levels as well as by introducing multifunctionalities. The functionalization of cellulose via use of several types of oxidation reagents can indeed lead to a wide variety of polymeric structures, with the following parameters: (i) type of functional groups incorporated, (ii) extent of functional groups incorporated, (iii) distribution of functional groups along the cellulosic polymer chain, (iv) the molecular weight distribution of the resulting oxidized cellulose, (v) particle size distribution (and whether nanofibers or nanoparticles are formed), (vi) morphology of the resulting oxidized cellulose, and (vii) solubility in aqueous/non-aqueous media. Such explosive variety of new structural features can in turn provide an array of properties to cellulose, which can be a sustainable source of multifunctional polymers and nanosized materials.

It was observed that aldehyde, carboxy, and amine functionalized wood cellulose as reinforcements in epoxy composites shown interesting advantages as compared to the use of unfunctionalized (See "Curing characteristics of epoxy resins filled with cellulose and oxidized cellulose, A. J. Varma et al., Angew. Makromol. Chem., (1984), 122, 211-218)

As observed for other cellulose nanoparticle derivatives, spherical shapes are more likely to show stability in solvent dispersions as compared to nanofibers. Similarly, the geometrical shape of the nanoparticle can play a role in drug delivery and biomedical applications.

The carboxycellulose nanoparticles (6CC-NP and TCC-NP) are found efficient in stabilizing the dispersion of carbon nanotubes (SWCNT: single-walled carbon nanotubes and MWCNT: multi-walled carbon nanotubes) in aqueous media.

To overcome the technical constraints such as slow rate of oxidation or degradation, expensive reagent, poor solubility, slow reaction rate, poor yield, large particle size due to high molecular wt. cellulose, less carboxy content the present inventors have developed a process for synthesis of nano structured oxidized cellulose from lower molecular weight and lower crystalline cellulose derived from sugarcane bagasse (94% α-cellulose) as well as cotton linters of relatively high molecular weights and successfully prepared a long series of mono- and multi-oxidized celluloses and their nanoparticles having a variety of functional groups (dialdehyde, monocarboxy, dicarboxy, tricarboxy, and carboxy-dialdehyde) in different combinations and contents, as well as their solubility behavior in organic solvents and dilute aqueous alkaline solutions. Further the inventors have employed cheap and efficient oxidizing agent to reduce the degradation with achieving substantial carboxy content of the product and yield, and obtain the product in a form that produces spherical shaped nanoparticles in a narrow size distribution of 25-35 nm and low molecular weight of 50-70 DP (degree of polymerization). Thus the instant invention is economically significant, industrially feasible and environmentally non-hazardous, and produces the product in a new form which has never been reported before for carboxycellulose, i.e. spherical shaped nanoparticles in a narrow size distribution of 25-35 nm and, low molecular weight of 50-70 DP (degree of polymerization).

Therefore, the objective of the instant invention is to provide a new process to obtain spherical/circular nano-sized oxidized cellulose from non-wood cellulose under suitable condition for wide applications.

Further carboxy cellulose product has wide applications as anti-microbial material for use in wound dressing gauze, hemostatic material, biocompatible material, biocomposites, detergent builder, catalyst, ion-exchange resin, polymer platform for making other functionalized nanoparticles of cellulose such as hydrophobic cellulose nanoparticles, etc.

U.S. Pat. No. 7,662,801 (Kumar et al) reported use of a series of oxidized cellulose esters as a drug carrier in the development of biodegradable controlled and/or sustained release pharmaceutical, agricultural, and veterinary compositions, whereas Anderson et al. in Science 104 (2700), 301 (1946) reported substantial use of oxidized cellulose in surgery of uterus, in both cases the source of the cellulose is either softwood or hardwood pulp or cotton. Additionally mechanism of the antibacterial action of mono carboxycellulose and other ion-exchange derivatives of cellulose" reported in *Antibiot Med Biotekhnol*. 1986 August; 31(8): 624-8 by Abaev IuK. Further In vitro antimicrobial activity of oxidized regenerated cellulose against antibiotic-resistant microorganisms is disclosed in *Surg Infect (Larchmt)*. 2003 Fall; 4(3):255-62 by Spangler D et al.

Moreover, Jarmila Vytrasova et al. (J. Ind Microbiol Biotechnol (2008) 35; 1247-1252) discloses antimicrobial properties of oxidized cellulose (6-carboxy cellulose) and its salt in linter (-L) and microsphere (-M) from OKCEL (textile form of oxidized cellulose) and tested against a spectrum of microbial strains: *Escherichia coli, Pseudomonas aeruginosa, Staphylococcus epidermidis, Bacillus licheniformis, Aspergillus niger, Penicillium chrysogenum,*

*Rhizopus oryzae, Scopulariopsis brevicaulis, Candida albicans* and *Candida tropicalis* exhibited antimicrobial activity in the range of 0.1-3.5% w/v.

However, Cellulosic compounds have never been reported to be effective against bacterial species such as *Mycobacterium tuberculosis* (TB). These have potential to be used as inexpensive and safe drugs, as cellulose and its derivatives have been used in food products.

Further the linear 6-carboxy celluloses are known to be easy to make since celluloses are themselves linear and their use in wound dressings are well known. The anti-microbial activity of spherical/circular nanoparticles of carboxy cellulose against *Bacillus, Staphylococcus aureus, Mycobacterium* has been demonstrated Therefore, the present inventors have analysed the antimicrobial activity of the carboxycellulose, and accordingly developed pharmaceutical composition comprising of nano sized spherical/circular shaped carboxycellulose derivatives that significantly inhibits the growth of microbes.

OBJECTIVE OF THE INVENTION

The main object of the present invention is to provide an improved for the preparation of spherical shaped nanostructured carboxy cellulose with high carboxy content and high yield.

Another object of the present invention is to oxidize non-wood, lignocellulose, sugarcane bagasse derived α-cellulose and cotton cellulose to carboxy cellulose wherein the particle size of synthesized carboxy cellulose is in the range of 1-100 nm.

Another object of the present invention is to oxidize non-wood, lignocellulose, sugarcane bagasse derived α-cellulose and cotton cellulose to carboxy cellulose wherein the molecular weight of synthesized carboxy cellulose is in the range of 50-70 DP (degree of polymerization).

Another object of the present invention is to provide pharmaceutical composition comprising of nanostructured oxidized/carboxy celluloses, preferably 6-carboxy cellulose and 2,3,6-tricarboxycellulose by themselves or in association with one or more pharmaceutically acceptable carrier(s) or excipient(s) for treatment of microbial infections.

Another object of this study is to provide a suitable aqueous medium containing the spherical nano-shaped carboxycelluloses for stabilizing SWCNT and MWCNT's.

SUMMARY OF THE INVENTION

Accordingly, the present invention provides spherical shaped nanostructured and carboxy celluloses with carboxy content in the range of 1.0% to 24% and molecular weight of 50-70 DP (degree of polymerization), wherein size of spherical carboxy cellulose is in the range of 10-100 nm.

In one embodiment of the present invention an improved process for the preparation of nanostructured and spherical carboxy cellulose with carboxy content in the range of 1.0% to 24% wherein the said process comprising the steps of;
a. oxidizing α-cellulose in the presence of 2:1 ratio (v/v) of 60-70% $HNO_3$ and 75-85% $H_3PO_4$ and $NaNO_2$ (1.2-1.6 w/v %) at temperature ranging from 30° C.-80° C. for reaction time of 1 hr to 48 hrs to obtain nanostructured 6-carboxycellulose;
b. optionally, oxidizing α-cellulose to 2,3,6 tricarboxycellulose.

In an embodiment of the present invention cellulose used in step (a) and (b) is derived from sugarcane bagasse or from cotton.

In an embodiment of the present invention cellulose the nanostructured carboxycelluloses is in the form of spherical nanoparticles.

In another embodiment of the present invention the size of nanoparticles of carboxy celluloses is in the range of 10-100 nm.

In another embodiment of the present invention the molecular weight of nanoparticles of carboxy celluloses is in the range 50-70 DP (degree of polymerization).

In another embodiment of the present invention oxidation of α-cellulose or cotton cellulose to 2,3,6 tricarboxycellulose in step (b) was carried out by subjecting α-cellulose to oxidation in presence of sodium metaperiodate to obtain 2,3 dialdehyde cellulose; and oxidizing 2,3 dialdehyde cellulose in presence of nitroso producing agent 60-65% HNO3 and 75-85% H3PO4 in 2:1 (v/v) ratio, accompanied by NaNO2 in (1.2-1.6%) at temperature in the range 30° C.-80° C. for reaction time 15-20 hrs to afford spherical nanostructured 2,3,6 tricarboxycellulose having carboxy content in the range 1-25% at C6 position of glucose unit of cellulose and in the range of 1-75% at C2 and C3 together of glucose unit of cellulose.

In another embodiment of the present invention the nanostructured carboxycellulose exhibits solubility in dilute alkali solution selected from 0.1-15% of NaOH and organic solvents selected from the group consisting of acetonitrile, dimethylacetamide, dimethyl sulfoxide, dioxane, acetone, methanol, ethanol, chloroform, dichloromethane, tetrahydrofurane, toluene, dimethylformamide, pyridine.

Still in another embodiment of the present invention a pharmaceutical composition comprises nanoparticles of carboxy cellulose according to claim 1, alone or along with one or more the pharmaceutically acceptable excipient(s) and/or vehicle(s), and/or carrier(s) useful for treating microbial infections wherein the bacterial species is selected from *M. tuberculosis, E coli, B. subtilis S. aureus*.

Still in another embodiment of the present invention a pharmaceutical composition alone or together with pharmaceutically acceptable excipient(s) and/or vehicle(s), wherein the MIC value is obtained in between 2-5 mg/ml.

Still in another embodiment of the present invention a method of inhibiting growth of microbes in mammals, comprising administrating nanoparticles of carboxy or oxidized cellulose according to claim 1, alone or together with pharmaceutically acceptable excipient(s) and/or vehicle(s).

Still in another embodiment of the present invention the microbes are selected from the group consisting of bacteria, virus, fungi, parasites, yeast, mould; preferably bacteria selected from group *M. tuberculosis, E coli, B. subtilis S. aureus*.

Still in another embodiment of the present invention use of carboxy cellulose according to claim 1, as anti-microbial material in wound dressing gauze, hemostatic material, biocompatible material, biocomposites, detergent builder, catalyst, ion-exchange resin, polymer and hydrophobic cellulose nanoparticles.

DESCRIPTION OF FIGURES

FIG. 1 depicts structures of various oxidized celluloses synthesized a) 6-carboxy cellulose (6CC), b) 2,3-dicarboxy cellulose (DCC), c) 2,3-dialdehyde cellulose (DAC), d) 2,3,6-tricarboxy cellulose (TCC) and e) 6-carboxy-2,3-dialdehyde cellulose (6C2,3DAC); where $R\!=\!CH_2OH$ or COOH FIG. 2 depicts overlapping FTIR spectra of cellulose and 6-carboxy celluloses (A) at 25° C. (B) at 40° C. (1) cellulose (2) 1 h (3) 3 h (4) 6 h (5) 12 h (6) 24 h (7) 48 h. Determined by (Ca-acetate method, USP 1995);

FIG. 3 depicts overlapping FTIR spectra of (A) (1) TCC (25:15) (2) TCC (15:15) (3) TCC (5:15); (B) (1) TCC (15:15) (2) after further oxidation with NaClO$_2$ (sodium salt of acid) (3) after acidification of sodium salt of acid; (C) DCC (15%); (D) 6C2,3DAC (15:9) (1) before deconvolution (2) after deconvolution;

FIG. 4 depicts SEM images (1000×) of 6CC with varying carboxyl content (reaction performed at different time period at 40° C. (A-G) and at 25° C. (H); (A) cellulose (B) 1 h (6.2% carboxyl content) (C) 3 h (13.2% carboxyl content) (D) 6 h (14.0% carboxyl content) (E) 12 h (14.3% carboxyl content) (F) 24 h (16.0% carboxyl content) (G) 48 h (17.0% carboxyl content) (H) 48 h (21.5% carboxyl content);

FIG. 5 depicts TEM images for 6CC nanoparticles for 48 h at 40° C. (II crop) at two magnifications (A) at 200 nm (B) at 50 nm; (C) photograph of stable nanoparticle suspensions in water for the 2$^{nd}$ crops of 24 h and 48 h reactions at 40° C.;

FIG. 6 depicts SEM images (×500) of TCC and 6C2, 3DAC (15:9) having different carboxyl content (A) TCC (5:15) (B) TCC (15:15) (C) TCC (25:15) (D) 6C23DAC (15:9);

FIG. 7 depicts TEM image of TCC (15:15), II crop at 100 nm magnification;

FIG. 8 depicts the % inhibition curve for *E. coli* by oxidized celluloses: 6CC (1)6CC-NP (2) TCC (3) TCC-NP (4) ampicillin;

FIG. 9 depicts the inhibition of *E. Coli* by (A) Cellulose (B) 6CC (C) 6CC-NP (D) TCC (E) TCC-NP after 6 h incubation at 37° C. on LB-agar plate;

FIG. 10 depicts the % inhibition curve for *Bacillus subtilis* by oxidized celluloses: 6CC (1) 6CC-NP (2) TCC (3) TCC-NP (4);

FIG. 11 depicts graph showing the % inhibition curve for *Mycobacterium tuberculosis* H37Ra (ATCC 25177). by oxidized celluloses 6CC (1) 6CC-NP (2) TCC (3) and TCC-NP (4);

FIG. 12 depicts graph showing the % inhibition curve for *S. aureus* by oxidized celluloses 6CC (1) 6CC-NP (2) TCC (3) TCC-NP (4);

FIG. 13 depicts (i) FTIR of (A) 6CC-NP, (B) cellulose; (ii) CP-MAS 13C solid state NMR (A) 6CC-NP, (B) cellulose; (iii) WAXRD of (A) 6CC-NP, (B) cellulose;

FIG. 14 depicts (i) SEM of 6CC-NP; (ii) Non-contact mode AFM images of 6CC-NP (A) corresponding height image, (B) corresponding 3D image rotated at 451; (iii) TEM of 6CC-NP; (iv) inhibition of *E. coli* by (A) cellulose, (B) 6CC, (C) 6CC-NP; (v) dispersion study of CNT (A) cellulose+MWCNT, (B) cellulose+SWCNT, (C) MWCNT+ 6CC (II crop; NP), (D) SWCNT+6CC (II crop; NP).

Abbreviations (6CC): 6-carboxy cellulose,
(DCC): 2,3-dicarboxy cellulose,
(DAC): 2,3-dialdehyde cellulose,
(TCC): 2,3,6-tricarboxy cellulose,
(6C-2,3DAC): 6-carboxy-2,3-dialdehyde cellulose
6CC-NP: 6-carboxy cellulose nanoparticles
TCC-NP: 2,3,6-tricarboxy cellulose nanoparticles
TEM: Transmission electron microscopy
SEM: Scanning electron microscopy In the present specification, the following words and phrases are generally intended to have the meanings as set forth below, except to the extent that the context in which they are used indicate otherwise.

The non-wood cellulose also referred as "lignocellulose", "sugarcane cellulose", "sugarcane bagasse".

The term "oxidized cellulose" is particularly related to "carboxy cellulose".

DETAILED DESCRIPTION OF THE INVENTION

The present invention provides an improved process for preparation of nanostructured carboxy cellulose with high carboxy content (1.0 to 24%) in good yield, from low molecular weight sugarcane bagasse derived α-cellulose; wherein the process comprises subjecting the sugarcane bagasse derived α-cellulose to oxidation at temperature ranging from 25° C. to 80° C. for reaction time 1 to 48 hrs.

The sugarcane bagasse is used as easy, renewable, non-wood cellulose source to derive lower molecular wt., lower crystalline α-cellulose In the instant invention the carboxy cellulose is selected from the group consisting of monocarboxy, dicarboxy, tricarboxy, carboxy-dialdehyde, dialdehyde cellulose or derivatives thereof, wherein the oxidization of sugarcane bagasse derived α-cellulose and cotton cellulose takes place at C2, C3 and C6 position of glucose unit of cellulose, either at single position or in combination thereof, in presence of oxidizing agent selected from the group consisting of nitroso radical producing agent, sodium metaperiodate, and sodium chlorite.

The array of carboxy cellulose is not limited to 6-carboxy cellulose (6CC); 2,3-dicarboxy cellulose (DCC); 2,3,6-tricarboxy cellulose (TCC); 6-carboxy-2,3-dialdehyde cellulose (6C2,3DAC); and 2,3-dialdehyde cellulose (DAC).

The structural representation of said oxidized celluloses is depicted in FIG. 1.

The synthesized carboxy cellulose are in the form of nanofibres or nanoparticles having shape selected from spherical, circular and like thereof wherein the diameter of quasi spherical/circular nanoparticles is in the range of 1-100 nm.

The oxidation process is carried out at temperature ranging from 25° C. to 80° C. and reaction time in the range of 1 hr to 48 hrs.

The carboxy content of oxidized celluloses is obtained in the range of 1.0% to 24%, where the yield of carboxycelluloses is more than 50%.

The carboxy cellulose are selected from the group consisting of 6-carboxycellulose and 2,3,6-tricarboxycellulose having smaller particle size and high carboxy content.

The present invention provides synthesis of nanoparticles of 6-carboxycellulose having uniform size and significant carboxy content, based on oxidation of sugarcane bagasse derived α-cellulose under suitable temperature and reaction time, wherein the oxidizing agent is niroso radical producing agent.

The nitroso radical producing agent is particularly an acid mixture of 65% HNO$_3$ and 85% H$_3$PO$_4$, in 2:1 ratio (v/v) accompanied by NaNO$_2$ in the range of (1.0-1.5 w/v %). The presence of nitroso radical as oxidizing agent makes fast the rate of degradation. The suitable temperature is in the range of 30° C. to 70° C. and reaction time is in the range of 1 hr to 48 hrs.

Particularly the oxidation reaction is performed at four different temperatures, 25° C., 40° C., 50° C., and 70° C. for various time intervals (1 h, 3 h, 6 h, 12 h, 24 h and 48 h) to obtain 1$^{st}$ crop and subsequent 2$^{nd}$ crop. The carboxy content and yield of 6-CC vis-à-vis temperature is given in Table 1. Subsequently the purification or washing of the crop is carried out in presence of polar solvents such as acetone, ethanol, methanol, butanol, n-propanol, isopropanol, water, ethyl acetate either alone or mixtures thereof.

The nanoparticles of 6 carboxy cellulose is obtained by oxidizing the cellulose at 40° C. for 1 to 48 hrs with carboxy content in an amount of 6.2 to 22%, particularly the nanoparticles of 6 carboxy cellulose with 21.5% carboxy content is obtained under 40° C. for reaction time 48 hrs.

TABLE 1

Percent carboxyl content, yield and DP of 6-carboxy celluloses at different temperatures and time periods (A)

| Time | —COOH Content (%) * | | | | Yield (%)/ DP | | | |
|---|---|---|---|---|---|---|---|---|
| (h) | 25° C. | 40° C. | 50° C. | 70° C. | 25 C. | 40° C. | 50° C. | 70° C. |
| 1 h | 1.7 | 6.17 | — | — | 84.0/87 | 83.0/86 | — | — |
| 3 h | 3.0 | 13.2 | — | — | 73.0/86 | 72.0 | — | — |
| 6 h | 8.6 | 14.3 | — | — | 71.0/84 | 68.0/81 | — | — |
| 8 h | — | — | — | 13.9 | — | — | — | 16.0*/50 |
| 12 h | 14.1 | 14.0 | 13.2 | — | 69.0/82 | 60.0/78 | 46.0*/70 | — |
| 24 h (I crop) (IIcrop)* | 19.7 | 16.0 18.0 | — | — | 63.0/79 | 25.0/775.0*/70 | — | — |
| 48 h (I crop) (II crop) * | 22.0 | 17.0 21.5 | — | — | 45.0/77 | 22.0/765.0*/70 | — | — |

NP = Nanoparticles

According to Tables 1 the series of 6CC's containing different extents of carboxy groups, ranging from 1.7% to 22% for the reaction at 25° C., and 6.2% to 21.5% for the reaction at 40° C., including nanoparticles obtained irk the second crop at 24 h and 48 h.

The above oxidation led to obtaining 1.7%, 3.0%, 8.6%, 14.1%, 19.7% and 22% carboxy content celluloses at 25° C., and 6.2%, 13.2%, 14%, 14.3%, 16%, 17%, 18%, and 21.5% carboxy content celluloses at 40° C. In addition, a 6CC sample is synthesized by a three step sequential oxidation at 25° C. which produced 24% carboxy content. Another reaction is carried out at 50° C./12 h which produced only nanoparticles. The DP's obtained are in the range 50-70.

Especially the oxidation of α-cellulose at C-6 position takes place at 40° C. and 24 h/48 h reaction period, produced nanoparticles in the $2^{nd}$ crop. To entirely produce only nanoparticles of 6-carboxycellulose the reaction is carried out at 50° C. for 12 h; the entire product is obtained in a single crop as gel-like material which is seen in TEM to be nanoparticles of 6-carboxycellulose, and similar in shape and size to the second crop of the 40° C./48 h reaction product, giving an yield of 20% nanoparticles having carboxyl content in the range of 12-14%. However the oxidized cellulose at condition of 12 h/25° C. and 12 h/40° C. did not show any nanoparticles.

Further the oxidation proceeds at C6 position, at 40° C. the fiber integrity undergoes continuous attrition with time, when finally at 24 h and beyond, nanoparticles are seen adhering to each other (FIG. 4 F,G). For the reaction, at 25° C., nanoparticles begin to form after 48 h (FIG. 4H).

It is apparent that the oxidation of cellulose carried out at temperature 25° C. for 1 hr to 48 hrs gives 6 carboxycellulose with carboxy content in the range of 1.3 to 24%, particularly the oxidation at 25° C. for 48 hrs afford 6 carboxy cellulose with carboxy content in an amount of 24%.

The reaction product obtained at 50° C. and 70° C. produced only one crop, which consisted entirely of spherical nanoparticles. The products were characterized for carboxyl groups by the well established Ca-acetate method (USP 1995). The $1^{st}$. crop was fibrous in nature and had sizes ranging from 2-10 μm. Where not mentioned in the table, only one crop is obtained, i.e., it is $1^{st}$. crop with sizes 2-10 μm unless specified as NP (nanoparticles).

The monocarboxy cellulose derived from low molecular weight non-wood cellulose leads to smaller particle size, wherein the diameter of the nanoparticles of 6CC is uniform in the range of 25 nm to 35 nm.

The 6-carboxy cellulose is additionally oxidized into 6 carboxy-2,3 dialdehyde cellulose in presence of sodium metaperiodate, particularly 6-carboxy cellulose having 15% carboxyl content, is oxidized at C-2 and C-3, by using the well-established procedure using sodium metaperiodate to produce 6 carboxy-2,3 dialdehyde cellulose (6C-2,3DAC), wherein the carboxy content of 6 carboxy-2,3 dialdehyde cellulose at C6 position of glucose unit of cellulose is nearly 9%; and at C2 and C3 together of glucose unit of cellulose is nearly 15%. Further the 6 carboxy-2,3 dialdehyde cellulose is characterized by the FTIR spectra.

The invention provides two-step process for facile synthesis of nanoparticles/nanofibres of 2,3,6 tricarboxycellulose based on oxidation of sugarcane bagasse derived α-cellulose, under suitable temperature and reaction time. wherein the process comprises a) subjecting sugarcane bagasse derived α-cellulose in to oxidation in presence of sodium metaperiodate to obtain 2,3 dialdehyde cellulose; and b) oxidizing 2,3 dialdehyde cellulose in presence of nitroso producing agent at ambient temperature and reaction time to afford 2,3,6 tricarboxycellulose in good yield and carboxy content.

According to this embodiment, the carboxy content of 2,3,6 tricarboxycellulose at C6 position of glucose unit of cellulose is in the range of 15 to 18%; C2 and C3 together of glucose unit of cellulose in the range of 5-25%; wherein the yield of 2,3,6 tricarboxycellulose is more than 60%, preferably in the range of 60-80%.

Further 2,3-dialdehyde celluloses of 5%, 15%, 25% dialdehyde content, are synthesized from sugarcane bagasse derived α cellulose by using sodium periodate ($NaIO_4$) as oxidizing agent according to reported methods (A. J. Varma, in Polymer Degradation and Stability 77 (2002) 25-27), Similarly the 2,3-dicarboxy cellulose is synthesized from 2,3-dialdehyde (15%) by using sodium chlorite ($NaClO_2$), which is known in the art (A. J. Varma in Polymer Degradation and Stability 49, (2), 1995, Pages 245-250).

The 2,3-dialdehyde celluloses and 2,3-dicarboxy cellulose are further characterized by FTIR (FIG. 3C).

According to the invention, 2,3,6 tricarboxycellulose (TCC) with three different constitutions (5:15, 15:15, 25:15, where the first number refers to the C2-C3 substituents and the second to C6 substituent) are synthesized from 2,3 dialdehyde cellulose in presence of nitroso source as oxidizing agent The nitroso radical is particularly derived from acid mixture of 65% $HNO_3$ and 85% $H_3PO_{4in}$ 2:1 ratio v/v. The acid to starting material (2,3 dialdehyde cellulose) mixture was maintained in the ratio of 1:14. Further the $NaNO_2$ reagent in the range of (1.0-1.5 w/v % preferably 1.4 w/v %) is added to the acidified mixture. The oxidation reaction is carried out at ambient temperature, preferably in the range of 25° to 35° C., for 15-20 hrs, more preferably 25° C. for 16 hrs.

With regard to FIG. 6, TCC (5:15, 15:15, 25:5) the fiber breakage is observed in 5:15; in 15:15 fiber breakage is accompanied by clustering of fibers and the 25:15 samples shows further fragmentation and clustering. TCC (15:15) show the presence of nanofibers, which on further modification gives TCC nanoparticles (FIGS. 6 and 7); on the other side 6C-2,3DAC (15:9) shows the molecules are present in sheet like morphology (FIG. 6 D).

The variation in the microstructure of these TCC molecules is an important aspect for studying structure-property relationships of the differently substituted carboxy groups along the polymer chain.

The solubility of all mono- and sequentially carboxy celluloses were studied in different concentrations of dilute alkali solution, preferably 0.2% to 10% concentration of NaOH (Table 3). Also the solubility of said carboxy celluloses were checked at 1% w/v in several organic solvents such as acetonitrile, Dimethylacetamide, Dimethyl sulfoxide, Dioxane, Acetone, Methanol, Ethanol, Chloroform, dichloromethane, tetrahydrofurane, toluene, dimethylformamide, pyridine.

In accordance with table 3 herein below it was concluded that all the carboxy celluloses soluble in dilute alkali solutions of different concentrations; wherein tricarboxycelluloses were soluble in DMSO and DMAc and exhibited swelling in dioxane, acetone, methanol, ethanol; 6-carboxy-2,3-dialdehyde-cellulose was soluble in acetonitrile.

The invention provides pharmaceutical composition comprising of spherical nanoparticles of carboxycellulose derivatives based on sugarcane bagasse derived α-cellulose by themselves or along with the pharmaceutically acceptable excipient(s) and/or vehicle(s) or/and carrier(s) useful for treating microbial infections.

The microbes or microorganisms are not limited to bacteria, virus, fungi, parasites, yeast, mould, preferably the microorganism is bacterial species selected from the group consisting of Mycobacterium tuberculosis H37Ra, ATCC 25177, E. Coli, (E. coli dH5 alpha ATCC 67874) Staphylococcus aureus (ATCC 6538P), Bacillus subtilis ATCC 10774; or virus species selected from DNA viruses.

The microbial infections are not restricted to tuberculosis, cancer, inflammation and sepsis.

pneumonia, pan-ophthalmitis, visceral abscess, or musculoskeletal infections, tissue necrosis, urinary tract infections, diarrhea, anemia.

Further the instant composition may be formulated in different dosage forms like solid, semi-solid, liquid or gaseous forms, such as tablets, capsules, powders, granules, ointments, syrup, solutions, injections, gels, spray, microemulsion, micropaticles/microspheres or nanoparticles/nanospheres. The general procedures for preparing such compositions are well known to those skilled in the art.

The pharmaceutical preparations may be made by means of conventional mixing, granulating, dragee-making, dissolving, lyophilizing processes depend upon the physical properties of the active ingredient used.

The excipients are not limited to fillers, binders, solubilizer, disintegrating agents, cross-linked polymer, flow-regulating agents, lubricants, and glidants.

The present invention rakes to administering 'an effective amount' of the 'composition of invention' to the subject suffering from cancer, tuberculosis, bacterial and other microbial infections, wherein subject is preferably mammal, more preferably human.

Accordingly, pharmaceutical compositions may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

The invention also provides methods of treating or inhibiting the growth of bacterial and viral species, comprises administering an effective amount of instant oxidized cellulose or its pharmaceutical salt in association with one or more pharmaceutical carriers.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

Further the instant pharmaceutical composition can be prepared optionally in combination with additional known antimicrobial agents.

The invention furnishes the use of instant oxidized cellulose NP for the preparation of medicament useful for treating or inhibiting the growth of pathogens such as M. tuberculosis, E coli, B. subtilis, Pseudomanas fluorescenes, S. aureus, P. aeruginosa and DNA viruses in a subject, wherein the subject is mammal.

The antimicrobial activity of the instant quasi-spherical nanoparticles of carboxy or oxidized cellulose, wherein the MIC value of the oxidized cellulose is in the range of 2.0-5.0 mg/ml or % (w/v), for 100% inhibition of bacterial growth. Particularly the minimum inhibitory concentration for controlling or inhibiting the growth of mycobacterium tuberculosis of nanoparticle of 6CC and TCC is in between 4-5 mg/ml or % (w/v), within 6 to 8 hrs.

Further instant pharmaceutical compositions are biocompatible, since celluloses are widely consumed.

Subsequently, the inventors were evaluated the anti-microbial properties, biodegradability characteristics, and cellulose enzyme hydrolysis characteristics of said carboxy celluloses also nano-oxidized celluloses in biocomposites. The carboxy cellulose product has applications as anti-microbial material for use in wound dressing gauze, hemostatic material, biocompatible material, biocomposites, detergent builder, catalyst, ion-exchange resin, polymer platform for making other nanoparticles of cellulose such as hydrophobic cellulose nanoparticles, etc.

It was also demonstrated that these spherical functionalized nanoparticles are extremely efficient in stabilizing carbon nanotubes with minimal ultrasonication, thereby saving energy. Both these factors could be key development for paving the way to many new applications for this material. The efficiency of these carboxycellulose quasi-spherical nanoparticles in anti-microbial applications was studied for E. coli (FIG. 3). It was found that the nanoparticles were more efficient than their larger sized analogs in eliminating E. coli from aqueous solutions.

The instant carboxy cellulose samples were characterized by (Perkin Elmer) FTIR Spectrum in transmission mode, between 450 to 4000 $cm^{-1}$. A total of 6 scans were taken per sample with a resolution of 4 $cm^{-1}$; Surface morphology of oxidized cellulose samples were studied using scanning electron microscope (SEM) with dual beam scanning electron microscope (FEI company, model Quanta 200 3D) operating at 30 kV.

The samples were loaded on stubs and sputtered with thin gold film to prevent surface charging and also to protect them from thermal damage due to electron beam. Transmission electron microscopy (TEM) studies of cellulose nanoparticles were carried out by using FEI-Technai $G^2$-20 instrument. A 10 μL aliquot sample of 1 mg of oxidized cellulose in 10 ml distilled water was mounted on freshly glow discharged carbon coated Cu grids (200 mesh, ICON Analytical, India) and iodometric titration to estimate the periodate consumption

EXAMPLES

Following are the Examples Given to Further Illustrate the Invention and Should not be Construed to Limit the Scope of the Present Invention.

Experimental

1. FTIR, C13-NMR, and Wide-Angle XRD;

6CCs were synthesized by using an acid mixture (65% $HNO_3$ and 85% $H_3PO_4$) with added $NaNO_2$ as an oxidant. The literature reports that the reaction is generally carried out at room temperature (20-25° C.), as this reaction is very sensitive to temperature, leading to depolymerization and degradation to smaller fragments at higher temperatures. However the current synthesis was carried out at 25° C., 40° C., 50° C. and 70° C. so as to re-visit the oxidized products obtainable at higher temperatures in a strongly acidic environment, with the aim of generating nanoparticles of lower DP and possibly spherical shape. Further, the inventors have used agricultural residues (sugarcane bagasse, in this case) as the source of cellulose (~94% a-cellulose content), made by the process described in (ZL200880111416.3), since these celluloses are of lower molecular weight (DP ~450) and lower crystallinity (~50%) than wood and cotton cellulose. A parallel set of experiments was carried out using cotton linters (DP ~1000, ~70% crystallinity, and ~100% a-cellulose content) to ascertain whether the methodology was applicable to all varieties of cellulose with different physical and morphological characteristics. The literature reports that the reaction is generally carried out at room temperature (20-25° C.), as this reaction is very sensitive to temperature, leading to depolymerization and degradation to smaller fragments at higher temperatures. However the current synthesis was carried out at higher temperature so as to re-visit the oxidized products obtainable at higher temperatures in a strongly acidic environment with new work-up procedures, with the aim of generating nanoparticles of lower DP and spherical shape (Table 1).

The products were characterized by FTIR, C13-NMR, and wide-angle XRD; they all show that the overall spectral features of the carboxy functionalized cellulose nanoparticles correspond to those of the starting cellulose even after reaction, with the carboxy functional groups at C6 clearly identified and corresponding changes in the original unreacted C6 peaks (FIG. 13).

2. SEM, TEM, and AFM Analysis:

The spherical morphology of 6CC nanoparticles was clearly seen in SEM, TEM, and AFM images (FIG. 14). TEM and AFM images of these nanoparticles show fairly uniform size of the particles in the range of 25-35 nm. The SEM image appears to show, discrete nanoparticles; however, the particle sizes are 90-110 nm, indicating that 3-4 molecules were agglomerated.

Furthermore, DLS shows the particle size to be ~132 nm with a very low polydispersity index (PDI) of 0.045. It is reported in the literature that DLS and TEM analysis generally do not match accurately. In a recent paper on quasi-spherical regenerated cellulose characterization, the TEM image showed particle sizes in the range of 90-110 nm, whereas the DLS measurements showed a range from 50-550 nm, with the peak maximum at 200 nm and a relatively high PDI of 0.215 (M. G. Adsul, et al. in Biomacromolecules, 2012, 13, 2890). This difference generally arises from the fact that TEM studies were carried out in dry form (a sample droplet evaporated on a TEM copper grid), while the DLS measurements are carried out in suspension and polymer molecules, which have a good chance to agglomerate. It is interesting to note that instant spherical shaped cellulosic nanoparticles have a much narrower PDI than that of the elongated cellulosic nanofibers. The DP of these particles was approximately 50 at 70° C., or 70 at 50° C.). These nanoparticles are highly efficient against E. coli (FIG. 14, iv) and they stabilized single-walled carbon nanotubes (SWCNT) and multi-walled carbon nanotubes (MWCNT) in aqueous solution for several days (FIG. 14, v).

Examples

Materials

Sugarcane bagasse cellulose containing ~94% α-cellulose and 0.08% residual lignin was prepared a method developed by us. The sugarcane bagasse was provided by Godawari Sugar Mills, Sameerwadi, Karnataka. The details are in the patent (A. J. Varma, China Patent ZL 200880111416.3, dated 9 Jan. 2013

Chemicals

Analytical grade nitric acid (65%), ortho-phosphoric acid (85.0%), sodium nitrite (98.0%), and calcium acetate (99.0%) were procured from Thomas Baker, Mumbai, India. Sodium metaperiodate (99.5%), sodium thiosulphate (99.5%), and sodium bicarbonate (99.5%) were obtained from S.D. Fine Chemicals, Mumbai, India. Soluble starch (Merck), sodium hydroxide, methanol GR grade, potassium iodide and potassium dichromate were purchased from Rankem, Mumbai, India. All chemicals were used without further purification.

Example: 1

Preparation of 6-carboxy Cellulose (6CC)

Cellulose (10 gm) was taken in a 2-neck round bottom flask, equipped with overhead teflon stirrer. 140 ml acid mixture in 2:1 ratio (v/v) of 65% $HNO_3$ and 85% $H_3PO_4$ was added slowly over a period of 5 minutes. The acid mixture was allowed to get absorbed in the cellulose for 10-15 minutes. To this was then added 1.96 gm of $NaNO_2$ (1.4 w/v %). As soon as the $NaNO_2$ was added, reddish fumes of $NO_2$ gas were evolved. To prevent escaping of $NO_2$ gas, the side neck of round bottom flask was plugged with a stopper. The reaction was performed at two different temperatures, 25° C. and 40° C., for various time intervals (1 h, 3 h, 6 h, 12 h, 24 h and 48 h). The reaction was quenched by adding distilled water (five times the volume of reaction mixture) and allowed to stand for half an hour. The solid residue obtained was the $1^{st}$ crop. The decanted portion was centrifuged at 12000 rpm to obtain a gel like material in two cases (Table 1); this gel like material was taken as the $2^{nd}$ crop. The $1^{st}$ crop and $2^{nd}$ crop, were continuously washed separately with 2:1 ratio of methanol and distilled water, until pH of the filtrate was neutral. Final washing was done by acetone and the products were dried in a lyophilizer. The $2^{nd}$ crop was obtained only for the 24 h and 48 h reactions at 40° C.

The above methods led to obtaining 1.7%, 3.0%, 8.6%, 14.1%, 19.7% and 22% carboxy content celluloses at 25° C., and 6.2%, 13.2%, 14%, 14.3%, 16%, 17%, 18%, and 21.5% carboxy content celluloses at 40° C.

The products were characterized for carboxyl groups by the well established Ca-acetate method (USP 1995) and by FTIR (FIG. 2). The FTIR shows the characteristic carboxyl peak at 1735 $cm^{-1}$, which increases corresponding to increases in oxidation levels, and concurrent decrease in —$CH_2$ stretching peak at 2850 $cm^{-1}$ was observed.

TABLE 2

| Dilution | | SBC | TCC 1 | TCCNP | 6CC 1 | 6CC NP | CON-TROL | INOC-ULUM |
|---|---|---|---|---|---|---|---|---|
| $10^6$ | 0.1 | >500 | >500 | >500 | >500 | >500 | >500 | >500 |
| | 0.5 | | 250 | 311 | 190 | 353 | | |
| | 1 | >500 | 96 | 125 | 118 | 145 | | |
| | 2 | >500 | 48 | 90 | 38 | 60 | | |
| | 3 | >500 | 6 | 26 | 18 | 22 | | |
| | 4 | >500 | 1 | 3 | 0 | 0 | | |
| $10^7$ | 0.1 | 107 | 110 | 117 | 118 | 142 | 102 | 125 |
| | 0.5 | | 41 | 35 | 45 | 51 | | |
| | 1 | 118 | 23 | 18 | 16 | 30 | | |
| | 2 | 125 | 12 | 16 | 14 | 17 | | |
| | 3 | 134 | 1 | 6 | 2 | 5 | | |
| | 4 | 142 | 0 | 0 | 0 | 0 | | |

Example: 2

Synthesis of Nanoparticles of 6-carboxy Cellulose (6CC)

The oxidation of cellulose at C-6 position at 40° C. and 24 h/48 h reaction period, produced nanoparticles in the $2^{nd}$ crop. Further the nanoparticles of 6-carboxycellulose was synthesized by carrying out the (example 1) reaction at 50° C. for 12 h; the entire product was obtained in a single crop as gel-like material which was seen in TEM to be nanoparticles of 6-carboxycellulose, and similar in shape and size to the second crop of the 40° C./48 hrs reaction product, giving an yield of 20% nanoparticles having 13.5% carboxyl content.

Example: 3

Preparation of 2,3-dialdehyde Cellulose (DAC) and 2,3-dicarboxycellulose (DCC)

The 2,3-dialdehyde celluloses of 5, 15, 25% dialdehyde content, were synthesized by using sodium periodate ($NaIO_4$), according to reported methods (Cellulosic diamines as reaction-incorporated filler in epoxy composites, A J Varma and V B Chavan, Cellulose, 1, 215-219 (1994), On the dual role of starch, cellulose and their dialdehydes as fillers and accelerators in tertiary amine catalyzed curing of epoxy resins, A J Varma, and Y K Jamdade, Carbohydr. Polym., 5, 309-316 (1985).

The 2,3-dicarboxy cellulose were synthesized from 2,3-dialdehyde (15%) by using sodium chlorite ($NaClO_2$). The products were characterized by FTIR (FIG. 3C).

Example: 4

Preparation of 2,3,6-Tricarboxycellulose (TCC)

2,3,6-Tricarboxycelluloses (5:15, 15:15, 25:15) were synthesized from 2,3-dialdehyde cellulose (5; 15, 25% carbonyl content). 10 gm of 2,3-dialdehyde cellulose was taken in 2-neck round bottom flask equipped with a magnetic stirrer and guard tube. To this add the acid mixture (2:1 v/v 65% $HNO_3$ and 85% $H_3PO_4$). The ratio of acid to the starting material was 1:14. The reaction mixture was allowed to stir for 10 minute, and then 1.96 gm of $NaNO_2$ (1.4 w/v %) was added. The reaction was allowed to proceed at 25° C. for 16 h and the reaction was then quenched by adding the distilled water (5 times the volume of the reaction mixture). The work up and drying procedure of the reaction is same as in the earlier case of 6-carboxy cellulose. Two crops were obtained. (Table 2) The products obtained were characterized by FTIR (FIG. 3A). The FTIR on deconvolution (FIG. 3A (inset)) shows two peaks at 1744 $cm^{-1}$, 1731 $cm^{-1}$ corresponding to C6 and C2, C3 carboxylic groups.

TABLE 3

Yields of TCC prepared with different percent carboxyl contents

| Sr.No. | TCC | Carboxyl (%) at C-6 | Carboxyl (%) at C-2 and C-3 | Yield (%) |
|---|---|---|---|---|
| 1. | (I crop) | 15 | 5 | 78 |
|  | (II crop) | 17 | 5 | 20 |
| 2. | (I crop) | 15 | 15 | 64 |
|  | (II crop) | 18 | 15 | 20 |
| 3. | (I crop) | 15 | 25 | 63 |
|  | (II crop) | 18 | 25 | 18 |

In order to further confirm the oxidation of 2,3-dialdehyde groups occurring simultaneously with C6 oxidation, the reaction products were subjected to further oxidation using $NaClO_2$ and work up was carried as reported for 2,3-DCC. The FTIR spectra on deconvolution show three peaks at 1744, 1731 $cm^{-1}$ similar to previous product (FIG. 3A).

Example: 5

Preparation of 6-carboxy-2,3-dialdehyde cellulose (6C-2,3DAC)

The 6-carboxy-2,3-dialdehyde cellulose (15:9) was synthesized from 6-carboxy cellulose (15% carboxyl content). The 6-carboxy cellulose was further oxidized at C-2 and C-3, by using the well established procedure using sodium metaperiodate, described in the above section. The products were characterized by FTIR (FIG. 3D) and iodometric titration to estimate the periodate consumption. The FTIR spectra of 6-carboxy 2,3-dialdehyde cellulose shows the C=O peak at 1731 cm$^{-1}$ with broad —OH peak at 3400 cm$^{-1}$. On deconvolution the FTIR spectra, two peaks at 1742 cm$^{-1}$ and 1722 cm$^{-1}$, corresponding to carboxyl and carbonyl group appears which clearly shows the presence of carboxyl and carbonyl group in 6-Carboxy 2,3-dialdehyde cellulose.

Example: 6

Method for Determining Carboxy Content

The carboxyl content of oxidized cellulose was measured according to the method described by United States Pharmacopoeia (USP 1995), known as the Ca-acetate method. A 0.5 gm of sample was taken and submerged in 50 ml of 2% calcium acetate solution for 30 minutes. The mixture is titrated with 0.1N NaOH (standardized) by using phenolphthalein as an indicator. The volume of NaOH used was corrected by a blank titration. The % carboxyl content in sample was calculated by following formula:

$$\text{Carboxyl Content}(\%) = \frac{N \times V \times \text{MW(COOH)} \times 100}{\text{Wt. of Sample (mg)}}$$

Where N is the normality of NaOH and V is the volume of NaOH used in titration

Example: 7

Solubility Studies in Aqueous Alkaline

The solubility of all mono- and sequentially oxidized cellulose derivatives were studied in different concentrations of alkali (NaOH) from 0.2% to 10% (Table 3). In case of mono functionalized oxidized cellulose (6CC), the 22% oxidized sample was easily soluble even at 0.2% alkali solution. DCC (15%) was soluble in 0.4% alkali solution while DAC (25%) was soluble in 10% alkali solution and 5% DAC was completely insoluble in 10% alkali solution. The multi-functionalized oxidized cellulose TCC and 6C-2,3DAC were easily soluble in 0.2% alkali solution. Thus, alkaline solubility is a good indicator of the extent of oxidation of cellulose.

TABLE 4

Solubility of carboxycelluloses in (a) aqueous alkali solutions. Solubility in NaOH was checked in 1% solution at different concentrations of NaOH, at room temperature.

| | | NaOH (%) | | | | |
|---|---|---|---|---|---|---|
| Sr. No. | Sample Name | 10 | 5 | 2 | 0.4 | 0.2 |
| 1 | 22% 6CC | ++ | ++ | ++ | ++ | ++ |
| 2 | 14% 6CC | ++ | ++ | ++ | ++ | + |
| 3 | 8% 6CC | ++ | ++ | ++ | + | -- |
| 4 | 3% 6CC | ± | -- | -- | -- | -- |
| 5 | 15% DCC | ++ | ++ | ++ | ++ | + |
| 6 | 25% DAC | ++ | ± | -- | -- | -- |
| 7 | 15% DAC | ± | -- | -- | -- | -- |
| 8 | 5:15 TCC | ++ | ++ | ++ | ++ | + |
| 9 | 15:15 TCC | ++ | ++ | ++ | ++ | ++ |
| 10 | 25:15 TCC | ++ | ++ | ++ | ++ | ++ |
| 11 | 15:96 C-2,3 DAC | ++ | ++ | ++ | ++ | ++ |

Example: 8

Solubility Studies in Organic Solvents

The solubility of all oxidized samples was checked in 1% w/v in several organic solvents (Table 4). The higher oxidized 6CC (22%) was partially soluble in DMSO while all the TCC samples were completely soluble in DMSO. Further, TCC was also shows soluble in DMAc on heating. Similarly, [6C2, 3DAC] was soluble in acetonitrile on heating. TCC also swelled in several solvents like dioxane, acetone, ethanol and methanol. The solubility or swelling of oxidized celluloses in several organic solvents can lead to their facile transformation by a variety of organic chemical reactions and result in several new products.

TABLE 5

Solubility of carboxycelluloses in organic solvents

| Sr. No. | Solvents (1% Soln.) | 22% 6CC | 15:15 TCC | 25:15 TCC | 15:5 TCC | 15:96C-2,3DAC |
|---|---|---|---|---|---|---|
| 1 | CH$_3$CN | -- | -- | -- | -- | + |
| 2 | DMAc | -- | + | + | + | -- |
| 3 | DMSO | ± | ++ | ++ | ++ | -- |
| 4 | Dioxane | -- | (S) | (S) | (S) | -- |
| 5 | Acetone | -- | (S) | (S) | (S) | -- |
| 6 | Methanol | -- | (S) | (S) | (S) | -- |
| 7 | Ethanol | -- | (S) | (S) | (S) | -- |
| 8 | CHCl$_3$ | -- | -- | -- | -- | -- |
| 9 | DCM | -- | -- | -- | -- | -- |
| 10 | THF | -- | -- | -- | -- | -- |
| 11 | Toluene | -- | -- | -- | -- | -- |
| 12 | DMF | -- | -- | -- | -- | -- |
| 13 | Pyridine | -- | -- | -- | -- | -- |
| 14 | 1,2-DCE | -- | -- | -- | -- | -- |

Symbols: (++) complete soluble, (+) soluble on heating, (±) partially soluble, (--) complete insoluble, (S) swelled.

Therefore, the low molecular weight non-wood celluloses can be used to produce a series of functionalized cellulose having a range of monocarboxy, dicarboxy, tricarboxy, dialdehyde and carboxy-dialdehyde functional groups with different extents of the functional groups, and the synthesis can be tailored to produce nanoparticles. Further developing the chemistry and technology of oxidation products of cellulose obtained from non-wood sources for sustainable development of chemicals, polymers, and high-tech materials can be feasible due to enhanced solubility of these materials in dilute aqueous alkali and organic solvents.

Example 9

**Antimicrobial Activity of Carboxycellulose Against *E. Coli***

The % inhibition determination of oxidized cellulose for *E. coli*-DH5 alpha via OD measurement at ~1×10⁶ cfu.

The percent inhibition of 6CC, 6CC-NP, TCC, TCC-NP was determined for *E. coli*-DH5 alpha, ATCC 67874. *E. coli* strain were streaked onto the appropriate media and incubated overnight at 37° C. Single colonies were selected and inoculated into 10 ml of sterile broth. Inoculated broth was incubated at 37° C. overnight under constant agitation. Overnight cultures were diluted 1:100 and 1:1000 in broth, resulting in 1×10⁶ and 1×10⁷ cfu, as confirmed by plating serial dilutions. A mass of 0.1, 0.5, 1.0, 2.0, 3.0, 4.0 mg of each sample were re suspended in LB broth-HIMEDIA to achieve a concentration of 1 mg/ml and autoclaved at 121° C. for 15 minute. The 198 μl of diluted samples were distributed to the first five well of a 96-well plate (the experiment was performed in triplicate). Next, three and two well of sterile 96-well plate were filled with inoculum and blank (containing inhibitor-Ampicillin) respectively. The 1% inoculation in all the samples was done with 2 μl of 0.94 OD (620 nm) freshly grown *E. coli* culture and allowed them to mix well. To check the inhibition effect of all the samples, parafilm sealed plate was incubated at 37° C. for 6 hrs. After 6 hrs, plate was taken out, and the absorbance was at 620 nm using SPECTRAMAX³⁸⁴ plate reader. The % inhibitions for different samples are shown in FIG. 8, which indicates maximum MIC value at concentration between 3.5-4 mg/ml.

Example 10

**MIC and CFU Determinations of Oxidized Cellulose for *E. coli* at 1×10⁶ and 1×10⁷**

Samples i.e. SBC, TCC1, TCCNP, 6CC1, 6CCNP were serially diluted at 1×10⁶ and 1×10⁷ cfu and inoculated in the LB agar plates for CFU. Plates were incubated in incubator at 37° C. for 6 h. MICs were determined visually as the lowest concentration, at which each of the triplicate wells was clear. The reported MIC is the lowest concentration in which growth was inhibited in three replicate experiments. The MIC value reported here for, the oxidized cellulose is 3.5-4.0% (w/v), against *E. coli* for all the oxidized cellulose, only after 6 h of incubation as shown in FIG. 8, which indicates maximum MIC value at concentration between 3.5-4 mg/ml.

The viable count (cfu/ml) of microorganisms after 1 day in presence of cellulose and in oxidized cellulose at different concentration (0.1 to 4.0% (w/v) determined by dilution method is depicted in (Table 1).

Example 11

**Antimicrobial Activity of Carboxy Cellulose Against *Bacillus subtilis* (Gram+ve Bacteria)**

The % inhibition determinations of Oxidized cellulose for *Bacillus subtilis*-DH5 alpha ATCC 10774) was done via OD measurement at ~1×10⁶ cfu. The compounds 6CC, 6CC-NP, TCC, TCC-NP were weighed according to their concentration to make final volume of 1 ml LB media (LB media containing 1% Dextrose) prepared and added to all weighed compounds to make a stock of compound concentration and autoclaved. The inoculums of *Bacillus Subtilis* were prepared by incubating 1% inoculated LB broth-HIMEDIA for 12-14 hrs at 37° C. After incubation, log phase culture of *bacillus subtilis* showed OD 0.94 with wavelength 620 nm.

A mass of 0.1, 0.5, 1.0, 2.0, 3.0, 4.0 mg of each sample were resuspended in LB broth-HIMEDIA to achieve a concentration of 1 mg/ml and autoclaved at 121° C. for 15 minute. The 198 μl of diluted samples were distributed to the first five well of a 96-well plate (the experiment was performed in triplicate). Next, three and two well of sterile 96-well plate were filled with inoculum and blank respectively. The 1% inoculation in all the samples was done with 2 μl of 0.94 OD (620 nm) freshly grown *B. subtilis* culture and allowed them to mix well. To check the inhibition effect of all the samples, parafilm sealed plate was incubated at 37° C. for 6 hrs. After 10 hrs, plate was taken out, and read the absorbance at 620 nm using SPECTRAMAX³⁸⁴ plate reader. The % inhibition for different samples is shown in FIG. 3, which indicates maximum MIC value at concentration between 4-5 mg/ml.

Example 12

**Antimicrobial Activity of Carboxy Cellulose Against *Mycobacterium tuberculosis***

The % inhibition determinations of Oxidized cellulose for *Mycobacterium tuberculosis* H37Ra (ATCC 25177) was done via OD measurement at ~1×10⁶ cfu. The percent inhibition of 6CC, 6CC-NP, TCC, TCC-NP was determined for *Mycobacterium tuberculosis*. The compounds 6CC, 6CC-NP, TCC, TCC-NP were weighed according to their concentration to make final volume of 1 ml M.Phili (Defined media) prepared and added to all weighed compounds to make a stock of compound concentration and autoclaved. The inoculums of *Mycobacterium tuberculosis* were prepared by incubating 1% inoculated M.Phili (Defined media) for 10-12 days with 150 rpm at 37° C. After incubation, log phase culture of *Mycobacterium tuberculosis* showed OD 0.94 with wavelength 620 nm.

A mass of 0.1, 0.5, 1.0, 2.0, 3.0, 4.0 mg of each sample were re suspended in M.Phili (Defined media) to achieve a concentration of 1 mg/ml and autoclaved at 121° C. for 15 minute. The 198 μl of diluted samples were distributed to the first five well of a 96-well plate (the experiment was performed in triplicate). Next, three and two well of sterile 96-well plate were filled with inoculum and blank containing inhibitor Rifampicin 0.00192 ug/ml respectively. The 1% inoculation in all the samples was done with 2 μl of 0.94 OD (620 nm) freshly grown *Mycobacterium tuberculosis* and allowed them to mix well. To check the inhibition effect of all the samples, parafilm sealed plate was incubated at 37° C. for 8 days. After 8 days, plate was taken out, and the absorbance was read at 620 nm using SPECTRAMAX³⁸⁴ plate reader. The % inhibition for different samples are shown in FIG. 5 and then XTT assay performed to check cell viability, which indicates maximum MIC value at concentration between 4-5 mg/ml.

Example 13

**Antimicrobial Activity of Carboxy Cellulose Against *Staphylococcus aureus***

The percent inhibition of 6CC, 6CC-NP, TCC, TCC-NP was determined for *Staphylococcus aureus* ATCC 6538P.

The compounds 6CC, 6CC-NP, TCC, TCC-NP were weighed according to their concentration to make final volume 1 ml LB media (LB media containing 1% Dextrose) prepared and added to all weighed compounds to make a stock of compound concentration and autoclaved. The inoculums of *Staphylococcus aureus* ATCC 6538P were prepared by incubating 1% inoculated LB broth-HIMEDIA for 12-14 hrs at 37° C. After incubation, log phase culture *Staphylococcus aureus* ATCC 6538P showed OD 0.94 with wavelength 620 nm.

A mass of 0.1, 0.5, 1.0, 2.0, 3.0, 4.0 mg of each sample were re suspended in LB broth-HIMEDIA to achieve a concentration of 1 mg/ml and autoclaved at 121° C. for 15 minute. The 198 μl of diluted samples were distributed to the first five well of a 96-well plate (the experiment was performed in triplicate). Next, three and two well of sterile 96-well plate were filled with inoculum and blank respectively. The 1% inoculation in all the samples was done with 2 μl of 0.94 OD (620 nm) freshly grown *Staphylococcus aureus* ATCC 6538P and allowed them to mix well. To check the inhibition effect of all the samples, parafilm sealed plate was incubated at 37° C. for 6 hrs. After 10 hrs, plate was taken out, and read the absorbance at 620 nm using SPECTRAMAX[384] plate reader. The % inhibition for different samples is shown in FIG. 12.

INDUSTRIAL ADVANTAGES

The instant process is feasible, cost-effective and industrially viable as it employs cheaper and easily accessible raw materials i.e. non-wood source, oxidizing agent, the rate of reaction is high due to high temperature. Further the instant carboxy celluloses having high carboxy content are biocompatible hemostatic material, and their nanoparticles have potential applications in several areas high performance material and preparation of other hydrophobic cellulose nanoparticles. The low molecular weight cellulose improves the solubility of oxidized derivatives in aqueous and non-aqueous solution. The instant carboxy cellulose having wide spectrum anti-microbial activity. It also provides activity against *Mycobacterium tuberculosis* bacteria, which are otherwise very difficult to annihilate/destroy.

The invention claimed is:

1. Spherical shaped Nanostructured carboxy cellulose characterised by
   a) carboxy content in the range of 1.0% to 24%;
   b) molecular weight of 50-70 degree of polymerization; and
   c) particle size in the range of 10-100 nm,
   said spherical shaped Nanostructured carboxy cellulose selected from 6-carboxycellulose and 2,3,6 tricarboxycellulose, said 2,3,6 tricarboxycellulose having carboxy content in the range of 1-25% at C6 position of glucose unit of cellulose and in the range of 1-75% at C2 and C3 together of glucose unit of cellulose, said spherical shaped nano structure carboxy cellulose prepared by a process comprising:
   a) oxidizing α-cellulose derived from sugarcane bagasse or from cotton in the presence of 2:1 ratio (v/v) of 60-70% $HNO_3$ and 75-85% $H_3PO_4$ and $NaNO_2$ (1.2-1.6 w/v %) at temperature ranging from 30° C.-80° C. for reaction time of 1 hr to 48 hrs to obtain nanostructured spherical 6-carboxycellulose;
   b) and/or, oxidizing α-cellulose derived from sugarcane bagasse or from cotton to 2,3,6 tricarboxycellulose by subjecting said α-cellulose or the product of step a) to oxidation in presence of sodium periodate to obtain 2,3 dialdehyde cellulose and oxidazing 2,3 dialdehyde cellulose in presence of nitoros producing agent, 60-65% $HNO_3$ and 75-85% $H_3PO_4$ in 2:1 (v) ratio, accompanied by $NaNO_2$ (1.2-1.6%) at temperature in the range of 30-80° C. for reaction time of 15-20 hours to afford nanostructured 2,3,6 tricarboxycellulose.

2. A pharmaceutical composition comprising nanoparticles of carboxy cellulose according to claim 1, alone or along with one or more the pharmaceutically acceptable excipient(s) and/or vehicle(s), and/or carrier(s) useful for treating microbial infections wherein the microbial infections are selected from the group consisting of bacteria, virus, fungi, parasites, yeast, mould, *M. tuberculosis, E coli*, and *B. subtilis S. aureus*.

3. A pharmaceutical composition according to claim 2, alone or together with pharmaceutically acceptable excipient(s) and/or vehicle(s), wherein the MIC value is obtained in between 2-5 mg/ml.

4. A method of inhibiting growth of microbes in mammals, comprising administrating nanoparticles of carboxy or oxidized cellulose according to claim 1, alone or together with pharmaceutically acceptable excipient(s) and/or vehicle(s).

5. A method of treating microbial infections, said method comprising a step of administering the pharmaceutical composition of claim 2.

6. An anti-microbial material comprising the spherical shaped nanostructured carboxy cellulose of claim 1, wherein the anti-microbial material is selected from the group consisting of wound dressing gauze, hemostatic material, biocompatible material, biocomposites, detergent builder, catalyst, ion-exchange resin, and polymer and hydrophobic cellulose nanoparticles.

7. The spherical shaped nanostructured carboxy cellulose according to claim 1, wherein the nanostructured carboxycellulose exhibits solubility in dilute alkali solution selected from 0.1-15% of NaOH and organic solvents selected from the group consisting of acetonitrile, dimethylacetarnide, dimethyl sulfoxide, dioxane, acetone, methanol, ethanol, chloroform, dichloromethane, tetrahydrofurane, toluene, dimethylformamide, and pyridine.

* * * * *

UNITED STATES PATENT AND TRADEMARK OFFICE
CERTIFICATE OF CORRECTION

PATENT NO. : 10,017,583 B2
APPLICATION NO. : 14/895590
DATED : July 10, 2018
INVENTOR(S) : Anjanikumar Jyotiprasad Varma et al.

It is certified that error appears in the above-identified patent and that said Letters Patent is hereby corrected as shown below:

On the Title Page

Item (57) Abstract Line 8, "in the range of 50-70" should be -- in the range of 50-70. --.
Item (57) Abstract Line 10, "comprising" should be -- comprised --.

In the Specification

Column 1,
Lines 16-17, "composition comprising" should be -- compositions comprised --.
Line 25, "large, fraction" should be -- large fraction --.

Column 2,
Line 7, "have" should be -- has --.
Line 22, "configuration also" should be -- configuration; also --.
Line 27, "was carried by" should be -- was carried out by --.
Line 28, "NaNO$_2$ led" should be -- NaNO$_2$ which led --.
Line 41, "1973" should be -- 1973. --.
Line 60, "gives" should be -- giving --.

Column 3,
Line 2, "published" should be -- (published --.
Line 25, "in to get" should be -- to get --.
Line 37, "of the uterus" should be -- of the uterus; --.
Line 60, "shown" should be -- showed --.
Line 61, "(See" should be -- (see --.
Line 64, "218)" should be -- 218). --.

Column 4,
Lines 54-55, "cellulose" reported" should be -- cellulose was reported --.

Signed and Sealed this
Fourth Day of September, 2018

Andrei Iancu
*Director of the United States Patent and Trademark Office*

Column 5,
Line 14, "demonstrated" should be -- demonstrated. --.
Lines 17-18, "comprising of nano sized" should be -- comprising nano-sized --.
Line 24, "improved" should be -- improvement --.
Line 38, "comprising of nanostructured" should be -- comprising nanostructured --.
Line 54, "In one embodiment of the present invention" should be -- One embodiment of the present invention is --.
Line 57, "steps of;" should be -- steps of: --.

Column 6,
Line 1, "In an embodiment of the present invention cellulose the" should be -- In an embodiment of the present invention, the --.

Column 7,
Line 38, "(ATCC 25177). by" should be -- (ATCC 25177) by --.

Column 8,
Line 20, "α-cellulose" should be -- α-cellulose. --.
Line 37, "carboxy cellulose" should be -- carboxy celluloses --.
Line 48, "are" should be -- is --.
Line 55, "niroso" should be -- nitroso --.

Column 9,
Line 33, "Tables" should be -- Table --.
Line 36, "irk" should be -- in --.
Line 53, "an yield" should be -- a yield --.
Line 65, "afford" should be -- affords --.

Column 10,
Line 1, "is" should be -- are --.
Line 5, "is" should be -- are --.
Line 39, "1st." should be -- 1st --.
Line 60, "time." should be -- time, --.
Line 62, "α-cellulose in to oxidation" should be -- α-cellulose to oxidation --.

Column 11,
Line 11, "77 (2002) 25-27," should be -- 77 (2002) 25-27. --.
Line 21, "are" should be -- is --.
Line 45, "were" should be -- was --.
Line 48, "were" should be -- was --.
Line 54, "celluloses soluble" should be -- celluloses were soluble --.
Lines 59-60, "The invention provides pharmaceutical composition comprising of spherical nanoparticles" should be -- The invention provides a pharmaceutical composition comprising spherical nanoparticles --.
Line 67, "is bacterial species" should be -- is a bacterial species --.

CERTIFICATE OF CORRECTION (continued)  
U.S. Pat. No. 10,017,583 B2

Column 12,
Line 6, "sepsis." should be -- sepsis, --.
Line 14, "micropaticles" should be -- microparticles --.
Line 20, "depend upon" should be -- depending upon --.
Line 25, "rakes to" should be -- relates to --.
Line 61, "or % (w/v), for 100% inhibition" should be -- or % (w/v), is effective for 100% inhibition --.

Column 13,
Lines 1-4, "Subsequently, the inventors were evaluated the anti-microbial properties, biodegradability characteristics, and ... of said carboxy celluloses also nano-oxidized celluloses in biocomposites." should be -- Subsequently the inventors evaluated the anti-microbial properties, biodegradability characteristics, and ... of said carboxy celluloses and also nano-oxidized celluloses in biocomposites. --.
Line 25, "were" should be -- was --.
Line 67, "a-cellulose" should be -- α-cellulose --.

Column 14,
Line 25, "show," should be -- show --.
Line 30, "analysis" should be -- analyses --.
Line 46, "C.)." should be -- C. --.
Line 59, "9 Jan. 2013" should be -- 9 Jan. 2013). --.

Column 16,
Line 4, "an yield" should be -- a yield --.
Line 18, "(1994), On" should be -- (1994), on --.
Line 22, "cellulose" should be -- celluloses --.
Lines 42-43, "The work up and drying procedure of the reaction is same as" should be -- The work up and drying procedures of the reaction are same as --.
Line 65, "was carried as reported" should be -- was carried out as reported --.

Column 17,
Lines 17-20, "On deconvolution the FTIR spectra, two peaks at 1742 $cm^{-1}$ and 1722 $cm^{-1}$, corresponding to carboxyl and carbonyl group appears which clearly shows the presence of" should be -- On deconvolution of the FTIR spectra, two peaks at 1742 $cm^{-1}$ and 1722 $cm^{-1}$ corresponding to carboxyl and carbonyl groups, appear which clearly show the presence of --.
Line 56, "were" should be -- was --.

Column 18,
Line 29, "shows" should be -- shown --.

Column 19,
Line 10, "were" should be -- was --.
Lines 16-19, "A mass of 0.1, 0.5, 1.0, 2.0, 3.0, 4.0 mg of each sample were re suspended in" should be -- Masses of 0.1, 0.5, 1.0, 2.0, 3.0, 4.0 mg of each sample were resuspended in --.
Line 61, "was" should be -- were --.

Column 20,
Line 4, "A mass of" should be -- Masses of --.
Line 40, "A mass of" should be -- Masses of --.
Line 41, "re suspended" should be -- resuspended --.
Line 54, "are" should be -- is --.

Column 21,
Line 9, "A mass of" should be -- Masses of --.
Line 10, "re suspended" should be -- resuspended --.

In the Claims

Column 21,
Line 42 (Claim 1), "Nanostructured" should be -- nanostructured --.
Line 48 (Claim 1), "Nanostructured" should be -- nanostructured --.

Column 22,
Line 1 (Claim 1), "nano structure" should be -- nanostructured --.
Line 13 (Claim 1), "oxidazing" should be -- oxidizing --.
Line 21 (Claim 2), "one or more the" should be -- one or more of the --.
Line 31 (Claim 4), "administrating" should be -- administering --.
Lines 49-50 (Claim 7), "dimethylacetarnide," should be -- dimethylacetamide, --.